US009393688B2

(12) United States Patent
Nawrat et al.

(10) Patent No.: US 9,393,688 B2
(45) Date of Patent: Jul. 19, 2016

(54) MANIPULATOR OF A MEDICAL DEVICE WITH AUXILIARY MOTOR AND ENCODER

(71) Applicant: FUNDACJA ROZWOJU KARDIOCHIRURGII IM. PROF. ZBIGNIEWA RELIGI, Zabrze (PL)

(72) Inventors: Zbigniew Nawrat, Zabrze (PL); Lukasz Mucha, Przemysl (PL); Kamil Rohr, Bytom (PL); Krzysztof Lis, Wilkowice (PL)

(73) Assignee: FUNDACIA ROZWOJU KARDIOCHIRURGII IM. PROF. ZBIGNIEWA RELIGI, Zabrze (PL)

( * ) Notice: Subject to any disclaimer, the term of this patent is extended or adjusted under 35 U.S.C. 154(b) by 0 days.

(21) Appl. No.: 14/837,086

(22) Filed: Aug. 27, 2015

(65) Prior Publication Data
US 2016/0059409 A1    Mar. 3, 2016

(30) Foreign Application Priority Data

Aug. 31, 2014    (EP) ..................................... 14182974

(51) Int. Cl.
*B25J 9/12*    (2006.01)
*B25J 9/10*    (2006.01)
*B25J 13/02*    (2006.01)
*G05G 9/047*    (2006.01)

(52) U.S. Cl.
CPC  *B25J 9/126* (2013.01); *B25J 9/106* (2013.01); *B25J 13/02* (2013.01); *G05G 9/04792* (2013.01); *A61B 2034/742* (2016.02); *Y10S 901/09* (2013.01); *Y10S 901/23* (2013.01)

(58) Field of Classification Search
CPC ............ B25J 9/106; B25J 9/126; B25J 13/02; G05G 9/04792; G05G 9/04737
See application file for complete search history.

(56) References Cited

U.S. PATENT DOCUMENTS 5,587,937 A    12/1996    Massie et al. .................. 364/578
5,847,528 A *  12/1998    Hui .......................... B25J 9/106
                                                          414/735

(Continued)

FOREIGN PATENT DOCUMENTS

CN    103111998 A    5/2013    ................. B25J 9/00
WO    WO 2005/091116 A1    9/2005    ................ G06F 3/00
WO    WO 2012/162000 A2    11/2012    .............. G05G 9/047

OTHER PUBLICATIONS

Extended European Search Report mailed Mar. 9, 2015 in corresponding European application No. 14182974.7.

*Primary Examiner* — Gerald McClain
(74) *Attorney, Agent, or Firm* — Renner Kenner Greive Bobak Taylor & Weber

(57) ABSTRACT

A medical device manipulator is a motion controller of a surgical device and includes a fixed platform mounted on an extension arm and a mobile platform connected to the fixed platform by three connecting assemblies. On the fixed platform are three motors with encoders. Each connecting assembly includes a first arch connector with a first end directly rigidly connected to the rotational shaft of the respective motor. A second end is connected by a joint to a first end of a second arch connector. The second end of the second arch connector has at its end a transverse arch arm and is connected to the mobile platform, on which an auxiliary motor is mounted. On a shaft of the motor is mounted a gripping part. The rotational axes of the second ends of the second arch connectors intersect with an axis of rotation of the shaft of the auxiliary motor.

4 Claims, 6 Drawing Sheets

(56) References Cited

U.S. PATENT DOCUMENTS

| | | | | |
|---|---|---|---|---|
| 5,893,296 A * | 4/1999 | Rosheim | G05G 9/04737 74/490.03 |
| 6,105,455 A * | 8/2000 | Rosheim | B25J 17/0266 74/490.03 |
| 6,417,638 B1 | 7/2002 | Guy et al. | 318/560 |
| 6,853,965 B2 | 2/2005 | Massie et al. | 703/6 |
| 7,249,951 B2 * | 7/2007 | Bevirt | G05G 9/04 345/156 |
| 7,411,576 B2 | 8/2008 | Massie et al. | 345/156 |
| 7,478,576 B2 * | 1/2009 | Rosheim | B25J 9/0048 74/490.01 |
| 7,480,600 B2 | 1/2009 | Massie et al. | 703/6 |
| 8,188,843 B2 | 5/2012 | Helmer et al. | 340/407.1 |
| 8,602,456 B2 * | 12/2013 | Bosscher | G05G 9/047 74/471 XY |
| 2001/0000663 A1 | 5/2001 | Shahoian et al. | 345/156 |
| 2002/0097223 A1 | 7/2002 | Rosenberg | 345/157 |
| 2003/0030619 A1 | 2/2003 | Martin et al. | 345/156 |
| 2008/0028881 A1 * | 2/2008 | Sone | B25J 9/0048 74/471 R |
| 2009/0095108 A1 | 4/2009 | Payandeh et al. | 74/480 R |

\* cited by examiner

MANIPULATOR OF A MEDICAL DEVICE WITH AUXILIARY MOTOR AND ENCODER

THE INVENTION

The invention relates to a manipulator of a medical device, wherein said manipulator is a motion controller, for example, of a surgical device. Said manipulator is a control unit which allows to control motion between two structures, in particular dedicated to transferring motion of an operator into motion of a fixed-point medical robot, owing to which it is possible to control the position of the robot's arms, tool or an executive part of a tool in a work area while ensuring force feedback providing the operator with a subjective sense of contact between an object being controlled and an obstacle in the work area of the controlled object, wherein the force affecting the operator increases in line with the increased pressure of the controlled element on the obstacle.

STATE OF THE ART

In manipulators—motion controllers known to date there is a number of technical solutions which enable to control devices including medical robots.

US 2002/0097223 A1 discloses a motion controller in the form of device a joystick with a limited number of degrees of freedom and one force feedback on a turn around its own axis.

US 2003/0030619 A1 and US2001/0000663 A1 disclose control devices commonly called pads, wherein an operator works by moving a joystick and additional degrees of freedom are controlled by means of built-in keys-buttons. In this kind of a device feedback is achieved by making the whole controller (pad) vibrate, which vibrations are induced by micro vibration inductors (vibrators).

Moreover, WO 2005/091116 A1 discloses a solution, wherein feedback is achieved by means of deformable polymers in a magnetic field which increase pressure between cooperating, moving guide bars of a controller thus providing the user with a sense of force braking of the working part in motion.

Devices based on parallel structures and so-called Delta structures are also commonly applied as, for instance, the ones described in U.S. Pat. No. 8,188,843 B2, U.S. Pat. No. 6,853,965 B2, WO 2012/162000 A2 or U.S. Pat. No. 5,587,937. Said solutions differ in terms of drive transmission kinematics between the motor and the gripping element. There may be applied connectors wound on a drum as well as fixed in one point.

Differences also lie in control parts used. For example, U.S. Pat. No. 7,480,600 B2 discloses an invention, wherein an operator changes the position of the controller in a work area with three fingers.

Solutions disclosed, for example, in U.S. Pat. No. 6,417,638 B1 or U.S. Pat. No. 7,411,576 B2 are also gaining popularity. Said solutions have highly compact structures, serial kinematics and a limited number of degrees of freedom. The operator uses a gripping element in the form of a spline resembling a pen that he can manipulate in a specified area while excluding the area taken up by the controller.

Said designs are both bulky and elaborate in terms of the number of cooperating elements and units used to achieve force feedback. They are usually mounted to a table and the manipulation is performed within a limited range of motion of motion controllers' individual elements. The elaborate control system often causes significant delays between the controller and the controlled element. Counterweight or compensating springs are most often used to compensate for the gravitational load. Both approaches to generate forces and/or torques consist in generating loads in directions opposite to gravitational forces and/or torques.

Furthermore, CN 103111998 discloses a manipulator which is a motion controller comprising two platforms—a fixed platform and a mobile platform.

The fixed platform is a part of a motion controller devoid of all degrees of freedom and which remains immobile in relation to other subassemblies of the manipulator at work, that is while the mobile platform is moving. The mobile platform is a mobile element which can change its position in relation to the fixed platform by following trajectories in its work area. On the fixed platform there are three motors and encoders as measuring devices—rotational pulse transducers which enable to measure rotation angles. Lines going through rotational axes of motor shafts intersect at an angle of 60 degrees and form an equilateral triangle. Both platforms are connected by means of three connecting assemblies in the form of rods. Said connecting rods are mounted on both sides in the Cardan joint, which results in the possibility to perform two rotations on each side of the rod. Torque from the connecting rods is transferred onto the motor shaft by an intermediary element in the form of a semicircle pressed down by means of a strand. This requires sufficient tension of the strand, which results in elaboration of the entire mechanism. Kinematics based solely on Cardan joints results in limited mobility. Said controller is dedicated to work in only one position due to gravitational compensation in the gripping part. Said manipulator provides the user with force feedback, which means subjective sense of contact and force exerted on an element e.g. tool by generating sufficient force in a determined direction affecting the operator.

AIM OF THE INVENTION

The aim of the invention is to design a manipulator—motion controller which will enable mounting the construction in any chosen position and free control of the gripping part of the controller in such a way that motions of the operator do not meet obstacles in the form of parts of the device, thus providing the operator with a work area as large as possible, wherein he/she can manipulate the gripping part of the controller independently of the fastening thus minimizing the number of parts and weight. The invention is meant to provide the operator with a subjective sense of contact between the element being controlled and the obstacle in the work area of the controlled element, wherein the force and/or torque affecting the operator is proportionate to the force and/or torque exerted on the element controlled by the obstacle.

ESSENCE OF THE INVENTION

The invention relates to a medical device manipulator which comprises a fixed platform mounted on an extension arm and a mobile platform connected thereto by means of three connecting assemblies. On said fixed platform there are three motors with encoders built into the body thereof. The essence of the invention consists in the fact that lines comprising rotational exes of the shafts of the three motors intersect at one point at an angle of 120 degrees, and each assembly connecting the fixed platform to the mobile platform comprises a first arch connector with an angle range of 90 degrees whose first end is directly rigidly connected to the rotational shaft of a respective motor and a second end is connected by means of a joint with three degrees of freedom to the first end of the second arch connector. The second end of the second arch connector has at its end a transverse, arch arm by means of which it is connected by a joint to the mobile platform on which an auxiliary motor comprising an encoder is mounted, and on the shaft of said motor there is a directly or indirectly mounted gripping part. Rotational axes of the second ends of the second arch connectors intersect at one point on the line comprising the rotational axis of the shaft of the auxiliary motor mounted on the mobile platform.

The manipulator preferably comprises bumpers of first arch connectors and a spring element connected to the first arch connectors for mechanical compensation of relieving said first arch connectors.

The invention presents the functional construction of the manipulator—motion controller having control elements for many systems of coordinates of robot motion, wherein said robot can be mounted in any chosen manner which proves suitable for the operator. The construction of the motion controller enables adding additional degrees of freedom depending on the operator's needs. The mechanism also allows replacing individual subassemblies of the controller, thus providing the operator with the possibility to adjust and extend the range of motion of the gripping part in its work area. The manipulator's construction is simple and it allows to apply control with gravitational compensation of the controller, it also ensures fixed point of the trajectory for moving kinematic pairs. Additional bumpers and mechanical compensation of relieving first arch connectors render the manipulator more effective.

DESCRIPTION OF THE DRAWINGS

The invention has been presented in greater detail in the following embodiments shown in the drawing, where.

EMBODIMENT

Figure 1:
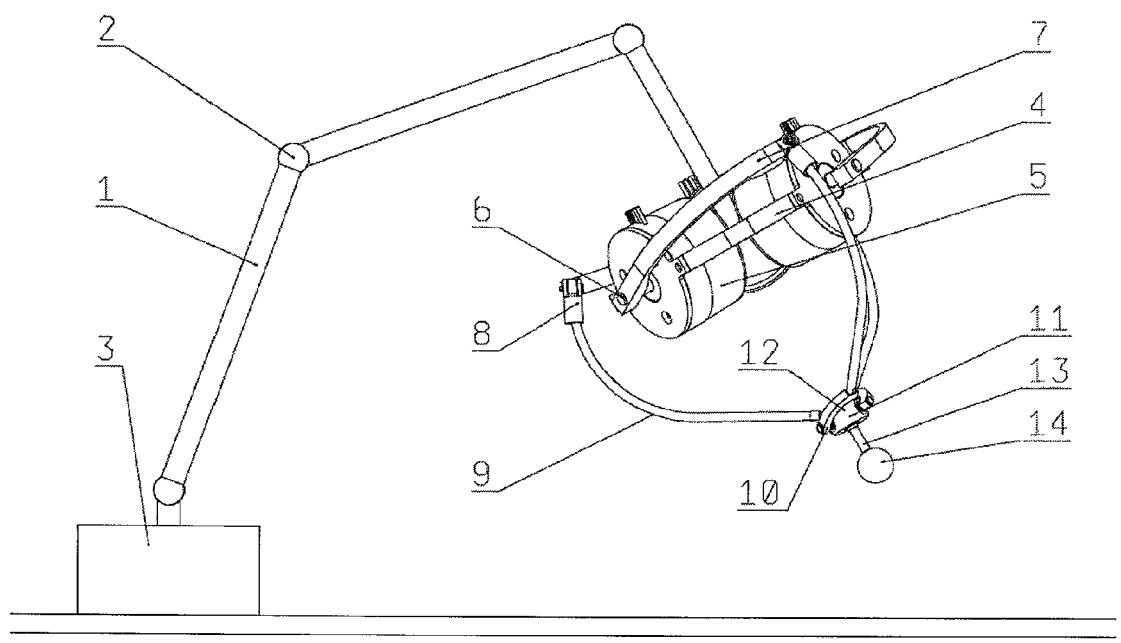
FIG. 1—a perspective view of the manipulator.
Figure 2:
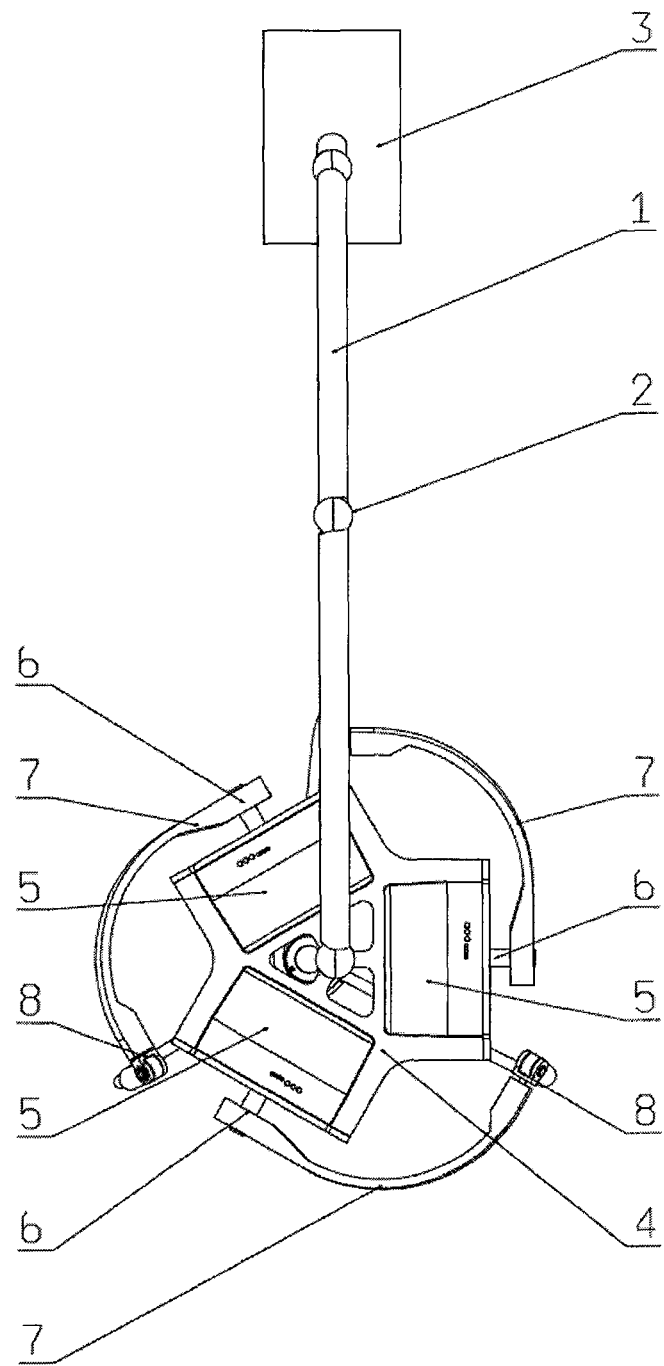
FIG. 2—a top view of the manipulator.
Figure 3:
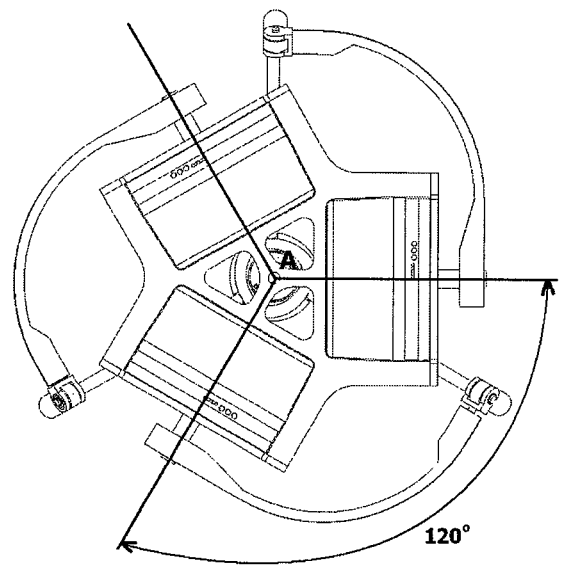
FIG. 3—a top view of the fixed platform with an indicated angle between the axes of the motors' shafts.
Figure 4:
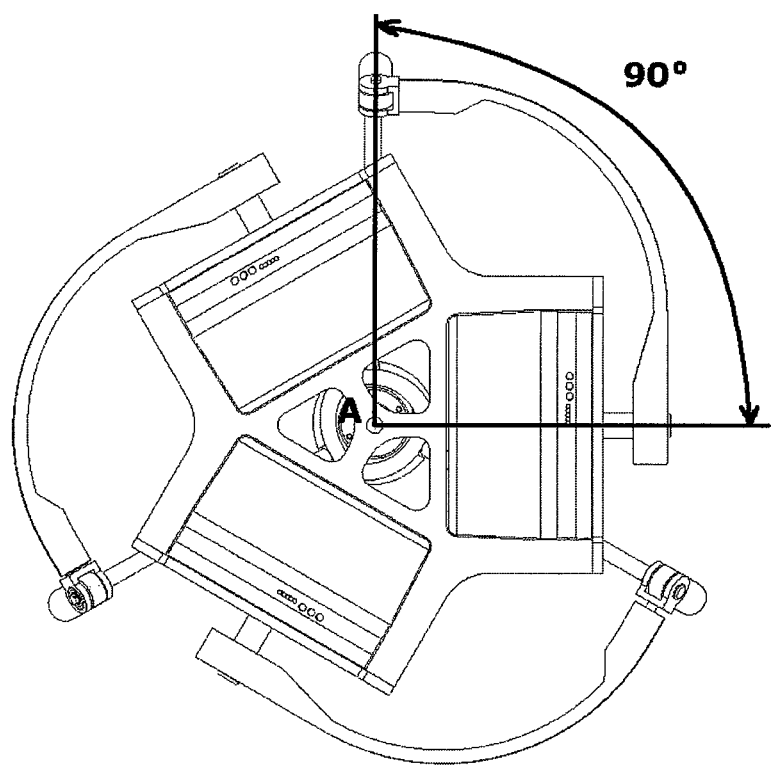
FIG. 4—a top view of the fixed platform with an indicated work angle of the first arch connectors.
Figure 5:
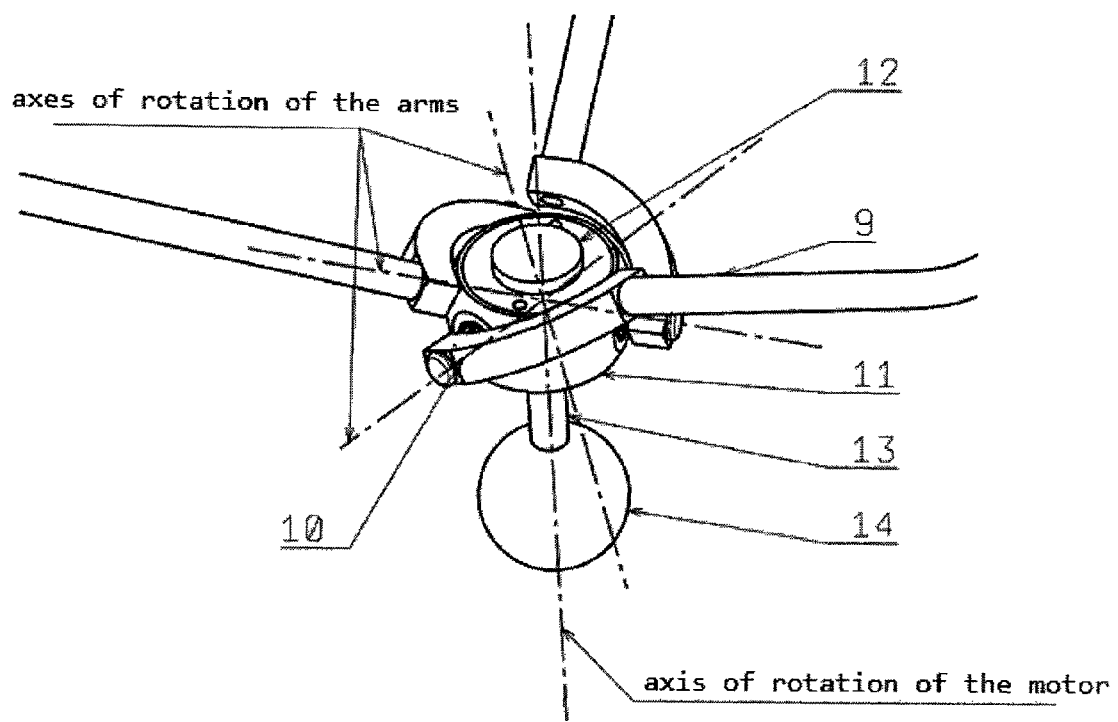
FIG. 5—a perspective view of the mobile platform with indicated rotational axes.

The manipulator according to the invention comprises a fixing arm 1 with any number of joints 2 enabling angular deflection and adjusting individual parts of the mounting system the user finds suitable. The fixing arm 1 is mounted to a base 3 in any way on one side, and to a fixed platform 4 on the other side. On the fixed platform 4 there are mounted three motors with built-in encoders 5. Lines comprising rotational axes of shafts 6 of the three motors 5 intersect at one point at an angle of 120 degrees (FIG. 3). On the shafts 6 of the motors 5 there are fixed first arch connectors 7 whose angle range is 90 degrees. The first arch connectors 7 are rigidly connected with their first ends to the shafts 6 of the motors 5, thus enabling rotation thereof, which results in angular deflection of a second end of the connectors 7. Said second ends of the first arch connectors 7 are connected by means of joints 8 with three degrees of freedom with first ends of second arch connectors 9. The three degrees of freedom are a result of a rotational connection of the joint 8 both to the first arch connector 7 and to the second arch connector 9. The angle range of 90 degrees of the first arch connectors 7 means such shape of said connector that the rotational axis of the joint 8 in relation to said connector 7 is at an angle of 90 degrees in relation to the rotational axis of the shaft 6 (FIG. 4). The second ends of the second arch connectors 9 have transverse arch arms (FIG. 5) and are rotationally connected with said arms by means of a joint 10 to a mobile platform 11. On the mobile platform 11 there is a motor mounted inside with a built-in encoder 12. A gripping part 14 for the operator or alternatively other subassemblies of the controller allowing to increase the number of degrees of freedom is mounted to the shaft 13 of the motor 12. The rotational axes of the second ends of the second arch connectors 9 intersect at one point (FIG. 5) on the line comprising the rotational axis of the shaft 13 of the auxiliary motor 12 mounted on the mobile platform 11.

Figure 8:
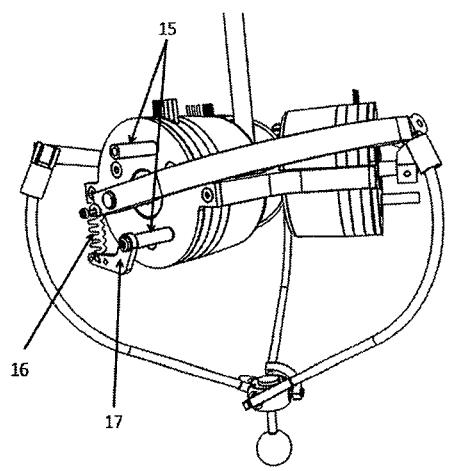
FIG. 8—the manipulator with optional accessories such as bumpers of the first arch connectors and compensation spring elements.

In another embodiment (FIG. 8) the manipulator comprises bumpers 15 of the first arch connectors 7 in the form of pins mounted to the bodies of the motors 5. The bumpers 15 mechanically limit and adjust the range of motion of the first arch connectors 7. Additionally for each first arch connector 7 there is a spring element—a spring 16 connected to the first arch connector 7 and an arm 17 fixed to the bumper 15, wherein said spring 16 is dedicated to mechanical compensation of relieving said first arch connectors 7.

Figure 6:
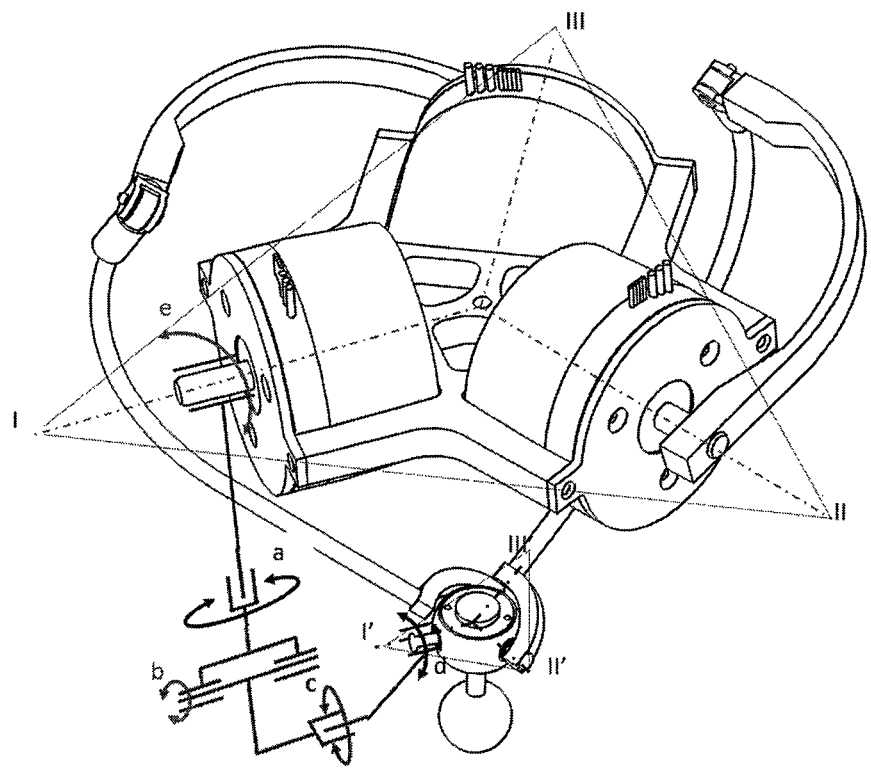
FIG. 6—a perspective view of the manipulator with indicated kinematics of motion of individual kinematic pairs.
Figure 7A:
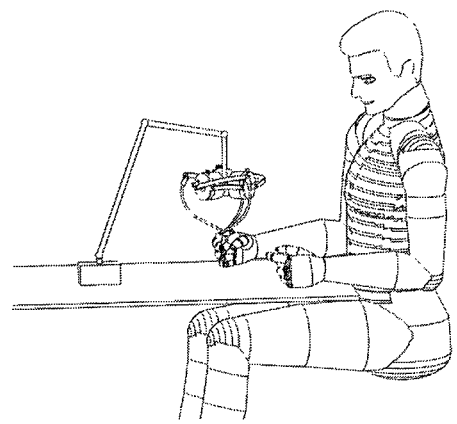
FIG. 7a to FIG. 7c—different work positions of the manipulator.
Figure 7B:
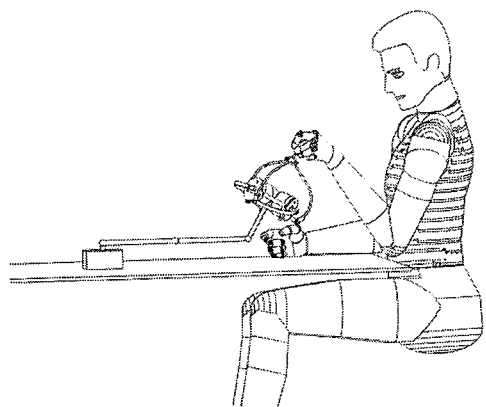
Figure 7C:
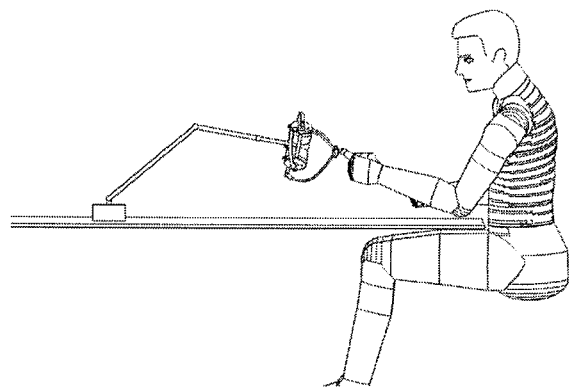

FIG. 6 schematically shows individual rotational pairs a, b, c, d, e of consecutive degrees of freedom. Motion from point I which is the vertex of a triangle formed on the fixed platform from points I, II, III determined by the rotational axes of the motors 5 to point I' which is the vertex of a triangle built on the mobile platform from points I', II', III' determined by rotational axes of the joint 10 on the mobile platform 11 is performed by the following kinematic pairs: a, b, c, d, e.

Changes in the angular position of the encoders are transformed, with the use of dedicated software and with assumed scaling, into motions of the operational tool mounted on the robot. Likewise, with the use of dedicated software, gravitational compensation and force feedback are achieved.

The invention claimed is:

1. A medical device manipulator comprising a fixed platform mounted on an extension arm and a mobile platform connected to the fixed platform via three connecting assemblies, wherein on the fixed platform there are three motors with encoders, characterised in that lines comprising rotational axes of shafts of the three motors intersect at one point at an angle of 120 degrees, and each connecting assembly comprises a first arch connector with an angle of 90 degrees, first end thereof is directly rigidly connected to the rotational shaft of the respective motor and second end thereof is connected via a joint with three degrees of freedom to a first end of a second arch connector, and a second end of the second arch connector has at its end a transverse arch arm and is connected via a joint to the mobile platform on which an auxiliary motor with an encoder is mounted, and on a shaft of said auxiliary motor there is a gripping part directly or indirectly mounted, and rotational axes of the second ends of the second arch connectors intersect at one point on a line comprising the rotational axis of the shaft of the auxiliary motor mounted on the mobile platform.

2. The manipulator according to claim 1 further comprising bumpers of the first arch connectors.

3. The manipulator according to claim 2 further comprising a spring element connected to the first arch connectors provided for mechanical compensation relieving of said first arch connectors.

4. The manipulator according to claim 1 further comprising a spring element connected to the first arch connectors provided for mechanical compensation relieving of said first arch connectors.

* * * * *